United States Patent
Busch et al.

(10) Patent No.: US 8,260,420 B2
(45) Date of Patent: Sep. 4, 2012

(54) METHOD AND DEVICE FOR PROCESSING CARDIAC SIGNALS

(75) Inventors: Ulrich Busch, Berlin (DE); Andreas Neumann, Berlin (DE); Ulrich Tietze, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 425 days.

(21) Appl. No.: 12/557,770

(22) Filed: Sep. 11, 2009

(65) Prior Publication Data

US 2010/0087886 A1    Apr. 8, 2010

(30) Foreign Application Priority Data

Oct. 8, 2008 (DE) .......................... 10 2008 042 681

(51) Int. Cl.
*A61N 1/368* (2006.01)
(52) U.S. Cl. ............................................ 607/17; 607/9
(58) Field of Classification Search .................. 607/2–9, 607/15–17
See application file for complete search history.

(56) References Cited

U.S. PATENT DOCUMENTS

| | | | |
|---|---|---|---|
| 5,179,949 A | 1/1993 | Chirife | |
| 5,330,507 A | 7/1994 | Schwartz | |
| 5,514,163 A | 5/1996 | Markowitz et al. | |
| 5,527,347 A * | 6/1996 | Shelton et al. | 607/9 |
| 5,549,647 A * | 8/1996 | Stoop et al. | 607/9 |
| 5,626,620 A * | 5/1997 | Kieval et al. | 607/9 |
| 2005/0137632 A1 | 6/2005 | Ding et al. | |
| 2005/0267539 A1* | 12/2005 | Betzold et al. | 607/9 |
| 2005/0288719 A1* | 12/2005 | Zhang et al. | 607/9 |
| 2007/0156194 A1 | 7/2007 | Wang | |
| 2008/0004665 A1 | 1/2008 | McCabe et al. | |
| 2008/0027492 A1 | 1/2008 | Sheldon et al. | |

FOREIGN PATENT DOCUMENTS

DE      44 06 877 A1    3/1994

OTHER PUBLICATIONS

European Search Report, dated Nov. 23, 2009, 8 pages.
German Search Report, dated Jun. 9, 2009.

* cited by examiner

*Primary Examiner* — Carl H Layno
*Assistant Examiner* — Allen Porter, Jr.
(74) *Attorney, Agent, or Firm* — ARC IP Law, PC; Joseph J. Mayo

(57) ABSTRACT

An electromedical implant having a far-field electrocardiogram detection unit connected or connectable to at least two implantable electrodes, at least one electrode of which is to be placed in the right atrium or right ventricle and is designed to record a far-field electrocardiogram via the terminal for the electrode to be placed in the right atrium or the right ventricle and one other electrode. The far-field electrocardiogram detection unit is connected to a far-field electrocardiogram evaluation unit, which is configured to detect signal features of the far-field electrocardiogram associated with an excitation or contraction of the left atrium and/or the left ventricle of the heart in a far-field electrocardiogram recorded by the far-field electrocardiogram detection unit.

5 Claims, 2 Drawing Sheets

METHOD AND DEVICE FOR PROCESSING CARDIAC SIGNALS

This application takes priority from German Patent Application DE 10 2008 042 681.4, filed 8 Oct. 2008, the specification of which is hereby incorporated herein by reference.

BACKGROUND OF THE INVENTION

1. Field of the Invention

The invention relates to a device and a method for processing cardiac signals, in particular an electromedical implant, e.g., a cardiac pacemaker, a cardioverter/defibrillator or the like as well as a method for operating such a device.

2. Description of the Related Art

Such implants are used in an essentially known manner to support or ensure adequate contraction of the chambers of the heart (ventricle and/or atrium) over time. Such electromedical implants are usually designed to detect natural contractions of the respective chamber by and evaluating the electric potential of the myocardium of the respective chamber associated with the natural contractions. The chart of these potentials is also known as an electrocardiogram, which is recorded between two electrically conductive electrodes, suitably arranged on or near the myocardium. Various types of electrocardiograms can be differentiated, depending on how and where the potential charts are plotted. If potential charts are detected by using a plurality of electrodes attached to the skin of the human body, this is called a superficial electrocardiogram. If the potential charts are detected with the help of an electronic implant and with the assistance of intracardiac electrodes connected to the implant, this is called an intracardiac electrogram. Of the intracardiac electrograms, near-field electrocardiograms can be differentiated from far-field electrocardiograms, depending on how far away the electrode recording the potential is from the site of excitation. The intracardiac detection may be accomplished in a bipolar manner, i.e., between two electrode contacts of an electrode line placed in the atrium or ventricle. As an alternative or in parallel with this, unipolar detection is also possible, i.e., between an electrode placed in the atrium or ventricle and a suitable mating electrode formed by the electrically conductive housing.

By recording electrocardiograms, natural (and also stimulated) excitation of the respective myocardium can be detected in an essentially known way. For example, the excitation of both ventricles is manifested in a strong signal segment of the respective electrocardiogram, known as the QRS complex. Excitation of the atrium is detected, for example, by detection of so-called P waves in the respective electrocardiogram. In this way, important events including the time of occurrence can be detected for control of an electromedical implant, in particular an implantable electrostimulator. Such events may be natural or stimulated atrial events, i.e., natural or stimulated excitation of the atrium resulting in a contraction of the atrium. Accordingly, the detected events may also be natural or stimulated events in the respective ventricle (right or left ventricle), i.e., natural or stimulated excitation of the respective ventricle with subsequent contraction.

Firstly, events thus detected in the heart are used to start certain timers in an implantable electrostimulator but also to detect certain intervals of time and to use them to control the electrostimulator. For example, by detecting a right-atrial natural event, (i.e., excitation of the right atrium), a timer may be started for a right-ventricular escape interval, at the end of which a right-ventricular stimulation pulse is delivered if a natural contraction of the right ventricle is not detected before the end of the right-ventricular escape interval. With so-called demand pacemakers, delivery of a ventricular stimulus is suppressed when a natural event is detected in the chamber that is otherwise to be stimulated during the course of a corresponding escape interval.

To adapt such a right-ventricular escape interval as accurately as possible to the needs of the individual heart, it is advantageous if the right-ventricular escape interval is adapted to a natural atrioventricular conduction time (AV delay) from the right atrium to the right ventricle and, as a rule, is only slightly longer than this AV interval.

It is likewise desirable to determine a suitable interval for the time lag between excitation of the left atrium and that of the left ventricle. In programming this time lag, it should be noted that active contraction of the left ventricle should occur approx. 100 ms after the left-atrial electric excitation (end of the left-atrial P wave), because the filling phase of the left ventricle is concluded only after approx. 100 ms. The start of the left ventricle contraction correlates with total excitation of the ventricular myocardium, as illustrated by a peak in the QRS complex in the superficial electrocardiogram.

With an electromedical implant for stimulation of the left ventricle, the corresponding AV time of the implant should also control mechanical synchronization between the left atrium and the left ventricle, so that contraction of the left ventricle does not begin before conclusion of the left-atrial ejection phase. The duration of the left-atrial ejection phase and/or the active filling phase of the left ventricle may be assumed to be a constant empirically determined value.

Electrodes in the right atrium and/or right ventricle are usually used to control the electromedical implant. For detection of atrial events with this so-called right-atrial electrode position, there is a conduction time between detection of the right-atrial natural event and/or right-atrial stimulation and the onset of the left-atrial ejection phase. However, the duration of this conduction time cannot usually be determined. The same thing is also true of the conduction time between a right-ventricular stimulus and the onset of the left-ventricular contraction, when ventricular events are detected with this so-called right-ventricular electrode position.

The latency times, which depend on the conduction times, are subject to interindividual variations and must therefore be measured individually on each patient.

BRIEF SUMMARY OF THE INVENTION

The object of one or more embodiments of the invention is to provide an electromedical implant and a method for operating same, which will make it possible to set a right-atrially initiated AV time of the implant for right-atrial stimulation as automatically as possible.

According to the invention, this object is achieved by an electromedical implant having a far-field electrocardiogram detection unit, said far-field electrocardiogram detection unit being connected or connectable, on the one hand, to at least one electrode to be placed in the right ventricle or the right atrium and, on the other hand, to the housing of the implantable medical device as a neutral electrode and being designed to record a far-field electrocardiogram via these electrodes. The far-field electrocardiogram detection unit is connected to a far-field electrocardiogram evaluation unit, which is in turn designed to detect signal features of a far-field electrocardiogram associated with excitation or contraction of the left atrium and/or left ventricle of the heart in a far-field electrocardiogram recorded by the far-field electrocardiogram detection unit.

The idea on which the one or more embodiments of the invention is based is thus to represent the total electric excitation of the atrium by using suitable intracardiac far-field leads. Points between which such a far-field electrocardiogram is derived as the positions of the electrodes used to record the respective far-field electrocardiogram are optimally selected here to span the entire excitation vector of the respective chamber of the heart. For example, excitation of the left atrium can be detected on the unipolar right-ventricular lead, and excitation of the right and left ventricles can be detected on the unipolar right-atrial lead accordingly.

This yields an electromedical implant and a method for operating same, which will automatically set a right-atrially initiated AV time of the implant for right-ventricular stimulation, so that exactly the time required for the left-ventricular filling phase between the end of the left-atrial P wave and the start of the left-ventricular contraction is exactly equal to the time required for the left-ventricular filling phase.

Accordingly, for detection of left-atrial contractions, a connection of the far-field electrocardiogram detection unit to an electrode to be placed in the right ventricle is provided, on the one hand, and also a connection to a neutral electrode in the form of an electrically conductive housing part of the electromedical implant is provided on the other hand.

For detection of left-ventricular contractions, the far-field electrocardiogram detection unit is preferably connected to an electrode provided for placement in the right atrium, on the one hand, and, on the other hand, to a neutral electrode in the form of an electrically conductive housing part of the electromedical implant.

In a preferred embodiment variant, the far-field electrocardiogram detection unit is connected or connectable, firstly, to an electrode for placement in the right ventricle and secondly to an electrically conductive outside surface of the housing of the electromedical implant, whereby the evaluation unit is designed to detect signal features of the far-field electrocardiogram associated with excitation of the left atrium of the heart and to determine an AS/AP delay value as the period of time between a detected natural or stimulated right-atrial event and the respective end of a left-atrial excitation in the far-field electrocardiogram. The AS/AP delay value is the period of time between detection of a natural event (AS) or, alternatively, also a stimulated right-atrial (AP) event, and the end of the left-atrial event, i.e., a type of interatrial latency time. For detection of a right-atrial event, the electromedical implant preferably has an essentially known atrial sensing unit connected or connectable to a sensing electrode for placement in the right atrium.

Additionally or alternatively, the far-field electrocardiogram detection unit may be connected or connectable, firstly, to an electrode for placement in the right atrium and, secondly, to an electrically conductive outside surface of the housing of the electromedical implant, and the evaluation unit may be designed to detect signal features of the far-field electrocardiogram associated with excitation of the left ventricle of the heart in a far-field electrocardiogram recorded in this way and to determine a VP delay value as the period of time between an effective right-ventricular stimulation pulse until a signal feature indicating the start of the left-ventricular contraction in the far-field electrocardiogram or up to a maximum in the far-field electrocardiogram. The VP delay is thus a type of interventricular latency time.

Furthermore, an electromedical implant designed as an electrostimulator for electric stimulation of one more chambers of the heart and having a stimulation control unit as well as at least one stimulation pulse generator, the latter being interconnected, such that the stimulation pulse generator generates electric stimulation pulses controlled by the stimulation control unit and delivers them at points in time determined by the stimulation control unit over an electrode line or a terminal for an electrode line, such that the stimulation control unit is designed to determine an AV time for the right-ventricular stimulation on the basis of the AS/AP delay and the VP delay.

The evaluation unit may also be designed to improve the signal-to-noise ratio of a left-atrial complex in the far-field electrocardiogram recorded by averaging the far-field electrocardiogram over several cardiac cycles and preferably by using the respective natural or stimulated atrial event as the reference point in time for the averaging.

The determination of an optimum AV time discussed above with the goal of an indirectly resulting delay between the end of the left-atrial excitation and the start of the left-ventricular excitation after right-ventricular stimulation preferably takes place as follows:

1. Firstly, the period of time (AS delay value) between detection of a natural right-atrial event and the end of the left-atrial excitation is determined in a far-field electrocardiogram, which has preferably been recorded by using a right-ventricular electrode and the housing of the implant as a neutral electrode.
2. Furthermore, the period of time (VP delay value) from delivery of a right-ventricular stimulus until detection of the onset of a left-ventricular contraction is determined in a far-field electrocardiogram, preferably recorded via a right-ventricular electrode and the housing of the implant as a neutral electrode. Instead of detecting the start of a left-ventricular contraction in the far-field electrocardiogram as the end point of a period of time to be determined, the point in time of detection of a maximum of the ventricular total excitation may also be detected as the end point of the period of time to be determined.
3. An average active filling phase (fill delay) is set at 100 ms, for example, i.e., at a value determined empirically.
4. The AV time to be determined after detection of a natural right-atrial event is then calculated as follows:

$$AV\text{ time} = AS\text{ delay} + \text{fill delay} - VP\text{ delay}$$

An optimum AV time setting after delivery of a right-atrial stimulus can be determined by analogy with determination of the AV time after a right-atrial event, merely triggered by the atrial stimulus (AP delay).

This method allows automatic setting of the AV time after A-sense and/or A-pace by detection of the interatrial latency times of the myocardium.

This method may be used for all dual-chamber and triple-chamber implants.

Other advantageous embodiments are derived by combination of the features described here with one another and with such features as are known from the prior art.

BRIEF DESCRIPTION OF THE DRAWINGS

Embodiments of the invention will now be explained in greater detail on the basis of an exemplary embodiment with reference to the figures, in which.

DETAILED DESCRIPTION OF THE INVENTION

Figure 1:
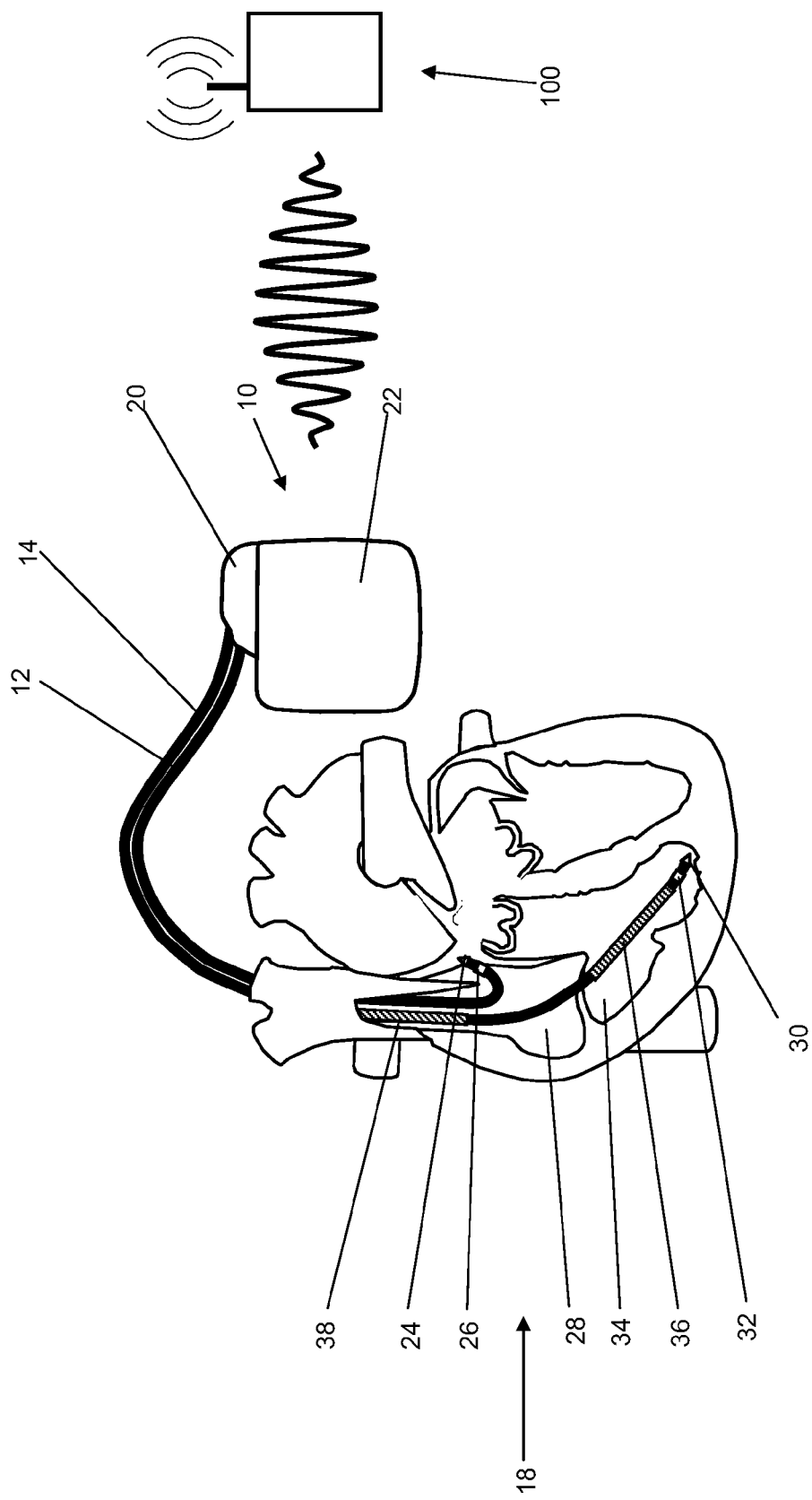
FIG. 1: shows a diagram of a biventricular cardiac stimulator with connected electrodes placed in the heart.

FIG. 1 shows an implantable cardiac stimulator 10 in the form of a dual-chamber cardiac pacemaker/cardioverter/ defibrillator with electrode lines 12 and 14 connected thereto and connected to the heart 18. Furthermore, an external device 100 is shown in the vicinity of the implantable cardiac stimulator 10. The electrode lines 12 and 14 are electrically connected to contact bushings in a header (terminal housing) 20 of the cardiac stimulator 10 via known standardized plug connectors. In this way, the electrode lines 12 and 14 are also connected to electronic components in the interior of a hermetically sealed metal housing 22 of the cardiac stimulator 10. These components are diagrammed schematically below in greater detail and determine the inventive functioning of the cardiac stimulator 10.

The electrode line 12 is a right-atrial electrode line and has an atrial tip electrode RA tip 24 at its distal end, and a short distance away from that, an atrial ring electrode RA ring 26, both of which are placed in the right atrium 28 of the heart 18.

The electrode line 14 is a right-ventricular electrode line and has a right-ventricular tip electrode RV tip 30 on its distal end, and in the immediate vicinity thereof, a right-ventricular ring electrode RV ring 32. The two electrodes are arranged in the apex of the right ventricle 34 of the heart 18.

Furthermore, the right-ventricular electrode line 14 also has a right-ventricular shock coil RV shock 36 as a large-area electrode for delivering defibrillation shocks. Another shock coil 38 is arranged in the superior vena cava and is therefore also referred to below as the SVC shock electrode.

Figure 2:
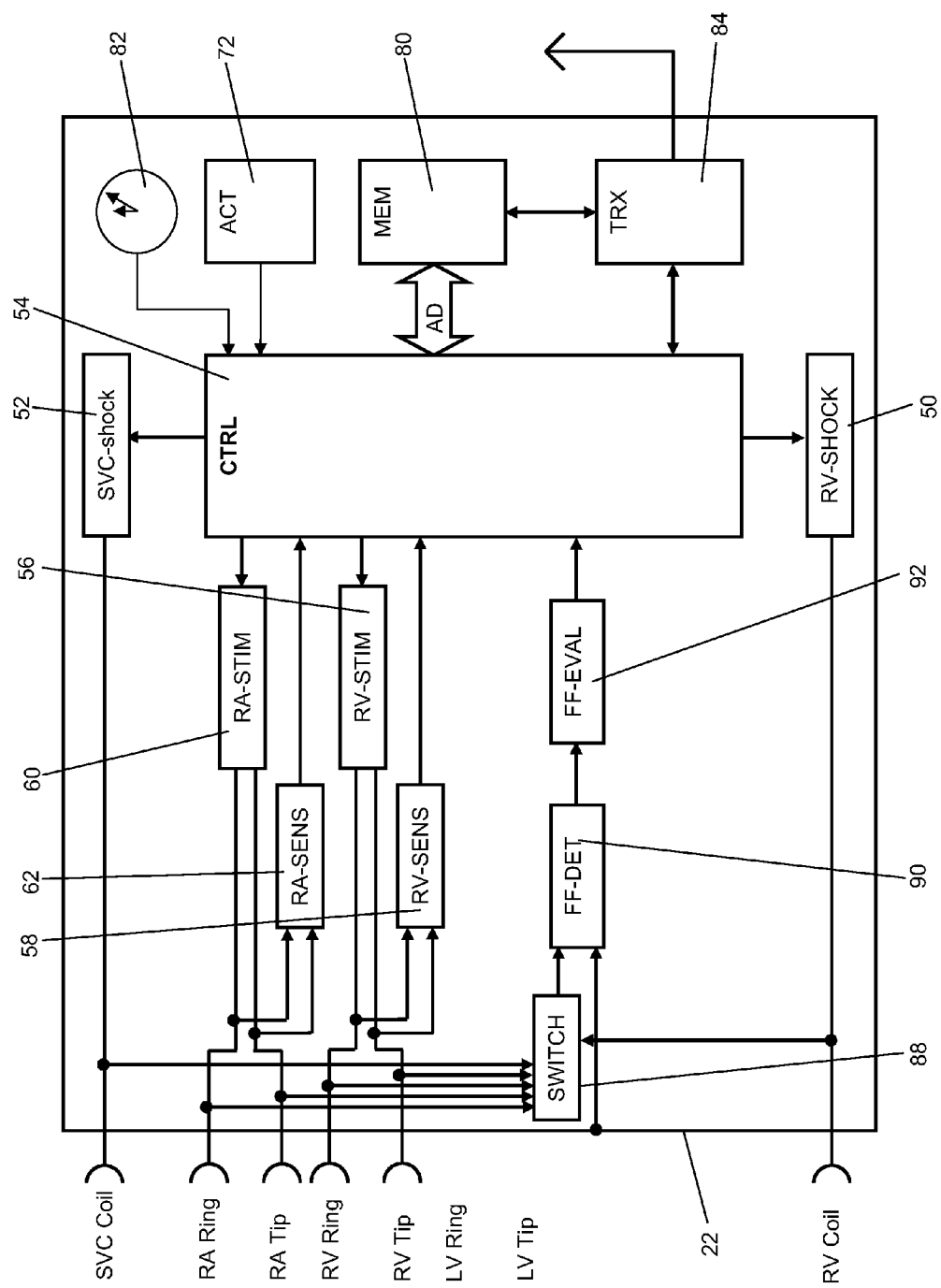
FIG. 2: shows a schematic block diagram of a cardiac stimulator.

FIG. 2 shows the main components of the cardiac stimulator 10. The electric terminals for the various electrodes 24, 26, 30, 32, 36 and 38 are shown on the left side. The shock electrodes 36 and 38 are each connected to a right-ventricular shock pulse generator 50 and/or SVC shock generator 52. The two shock generators 50 and 52 are each connected to a stimulation control unit 54, which triggers the two shock pulse generators 50 and 52 to generate and deliver a defibrillation shock on demand.

The terminal for the right-ventricular tip electrode RV tip and the terminal for the right-ventricular ring electrode RV ring are each connected to both a right-ventricular stimulation unit 56 and a right-ventricular sensing unit 58. Both the right-ventricular stimulation unit 56 and the right-ventricular sensing unit 58 are connected to the stimulation control unit 54.

The right-ventricular stimulation unit 56 is designed to generate a right-ventricular stimulation pulse in response to a trigger signal of the stimulation control unit 54 and to deliver it via the terminals of the right-ventricular ring electrode RV ring and the right-ventricular tip electrode RV tip. Alternatively, it is also possible for the housing 22 of the cardiac stimulator 10 to form a neutral electrode and for the right-ventricular stimulation unit 56 to be connected to the terminal for the right-ventricular tip electrode RV tip and housing 22 as another electrode for delivering a stimulation pulse. A right-ventricular stimulation pulse differs from a defibrillation shock in that the stimulation pulse has a much lower pulse intensity, so that it does not excite all the myocardial tissue of a chamber of the heart all at once as a defibrillation shock would do, but instead excites only the myocardial muscle cells in the immediate vicinity of the right-ventricular tip electrode RV tip 30. This excitation then propagates through natural stimulus conduction over the entire right ventricle 34 and thus ensures a stimulated contraction of the right ventricle 34.

The right-ventricular sensing unit 58 is designed to amplify and filter the electric potentials applied at the terminal for the right-ventricular ring electrode RV ring and the right-ventricular tip electrode RV tip through an input amplifier. In addition, the right-ventricular sensing unit 58 is designed to evaluate the characteristics of the electric signals applied at its inputs, such that the right-ventricular sensing unit 58 automatically detects a natural (intrinsic), i.e., automatic, contraction of the right ventricle 34. This may take place, for example, by comparing the characteristics of the signal applied at the inputs of the right-ventricular sensing unit 58 with a threshold value. The largest amplitude of the signal in the form of the so-called R wave is typically characteristic of a natural contraction of the right ventricle 34, which can be detected by threshold value comparison. The right-ventricular sensing unit 58 then delivers a corresponding output signal indicating a natural contraction of the right ventricle 34, to the stimulation control unit 54.

By a similar method, the terminal for the right-atrial tip electrode RA tip and the terminal for the right-atrial ring electrode RA ring are each connected to a right-atrial stimulation unit 60 as well as to a right-atrial sensing unit 62, which are in turn connected to the stimulation control unit 54. The right-atrial stimulation unit 60 is designed to generate stimulation pulses of an intensity sufficient to excite the right-atrial myocardium. The pulse intensity of the right-atrial stimulation pulses may be different from the right-ventricular stimulation pulses. The right-atrial sensing unit 62 is designed to detect a so-called P wave from the characteristic of the differential signal applied at its inputs, said P wave characterizing a natural (intrinsic) contraction of the right atrium 28. If the right-atrial sensing unit 62 detects a corresponding P wave, it generates an output signal, which it delivers to the stimulation control unit 54, characterizing a natural contraction of the right atrium 28.

As another component of the cardiac stimulator 10, an acceleration sensor 72 is connected to the stimulation control unit 54 and is integrated into the housing 22 of the cardiac stimulator 10. The acceleration sensor 72 is designed to detect a motion signal, depending on a patient's physical activity, and to output to the stimulation control unit 54 a corresponding first accelerometer output signal indicating the physical activity of the patient. This makes it possible for the stimulation control unit 54 to adapt the timing of the stimulation pulses to the patient's needs (hemodynamic demand).

In addition, the cardiac stimulator 10 comprises a memory unit 80, which is connected to the stimulation control unit 54 and makes it possible to save signals generated or evaluated by the stimulation control unit 54. On the other hand, the memory unit 80 makes it possible to save control programs for the stimulation control unit 54 in a modifiable form. Furthermore, the stimulation control unit 54 is connected to a timer 82.

The memory unit 80 is connected to a telemetry unit 84, making it possible to wirelessly transmit data stored in the memory unit 80 to the external device 100 or to transmit programming commands on the part of the external device 100 to the cardiac stimulator 10 and save them in the memory unit 80.

As a dual-chamber cardiac stimulator/cardioverter/defibrillator, the cardiac stimulator 10 is capable of stimulating the right atrium 28, the right ventricle 34 and the left ventricle 44 or just one or two of these chambers of the heart in a known way. This includes in particular stimulation of the respective heart chamber in demand mode, in which stimulation pulses are delivered to the respective chamber of the heart only if no intrinsic contraction of the respective chamber of the heart is detected by the respective sensing unit in a preceding respective escape interval. The cardiac stimulator 10 is thus capable of performing the known right-ventricular stimulation modes such as VVI, VVD or DDD.

For the timing of the stimulation pulses in the right-ventricular stimulation mode, the delay time by which a left-ventricular contraction follows a right-ventricular stimulation (VP delay) is ideally also taken into account.

To determine the implant-dependent interatrial time intervals for VDD and DDD stimulation, the cardiac stimulator 10 according to the invention has a far-field electrocardiogram detection unit 90, which can optionally be connected, on the one hand, to a right-ventricular electrode or a right-atrial electrode and, on the other hand, to the pacemaker housing 22 as a neutral electrode, so that the detected and processed potential is a unipolar cardiac potential. A switching unit 88 is provided for selection of a suitable electrode configuration to record a far-field electrocardiogram.

An evaluation unit 92 is connected to the output of the far-field electrocardiogram detection unit 90. The evaluation unit 92 is designed to evaluate the respective far-field electrocardiogram detected by the far-field electrocardiogram detection unit 90 and to detect signal features characteristic of left-atrial and/or left-ventricular excitation. Signal features characteristic of left-atrial excitation are detected in a far-field electrocardiogram recorded via a right-ventricular electrode and the housing 22 of the implant, and signal features characteristic of left-ventricular excitation are detected in a far-field electrocardiogram recorded via a right-atrial electrode and the housing 22 of the implant.

Accordingly, the evaluation unit 92 yields different output signals (markers) for left-ventricular and left-atrial events. The output signals (markers) for left-atrial events are used for non-recurrent or cyclic determination of the duration of interatrial conduction times.

To this end, the evaluation unit 92 may be designed to detect signal features characterizing the respective left-ventricular contraction and the respective left-atrial contraction on the basis of a comparison of morphology features of the respective current signal with stored morphology features. To do so, the evaluation unit 92 performs a wavelet transformation on the respective far-field electrocardiogram recorded by the far-field electrocardiogram detection unit 90 via the right-ventricular electrode or the right-atrial electrode and then compares the wavelet coefficients thereby recorded with comparative coefficients stored in a memory 80 to detect the respective left-atrial and/or left-ventricular contraction.

The evaluation unit 92 may also be designed so that the points in time of occurrence of the aforementioned morphology features within the stimulation cycle are determined only after adding up a certain number of individual heartbeats in the sense of a signal averaging technique.

The evaluation unit 92 is also designed to determine the duration of an AV time (AV delay) between excitation of the left atrium and a subsequent excitation of the left ventricle by the fact that the detection unit 90 determines the difference in time between the occurrence of a signal feature characterizing a left-atrial contraction or stimulation and the occurrence of a signal feature characterizing a left-ventricular contraction to be assigned to the left-atrial contraction.

The duration of the AV time on the left side may also be determined with the programming device. To do so, the corresponding electrograms or markers containing signal features are to be transmitted telemetrically from the pacemaker to the programming device. The detection unit is then part of the programming device. These measurements are then performed either automatically in the programming device or manually by displaying the electrograms or markers on the programmer's screen, freezing them and then measuring them by using calipers.

The evaluation unit may also be saved on the external device 100. Then the cardiac stimulator 10 is designed to telemetrically transmit the data describing the respective far-field electrocardiogram recorded by the far-field electrocardiogram detection unit 90 to the external device 100 by means of a telemetry unit 84.

The evaluation unit 92 is designed for determining an AV delay between the right atrium and the right ventricle while preserving an AV sequence on the left side that is optimum over time, such that the evaluation unit:

determines the period of time (AS delay) between the detection of a natural right-atrial event and the end of the left-atrial excitation in a far-field electrocardiogram, preferably recorded via a right-ventricular electrode and the housing of the implant as the neutral electrode;

determines the period of time (VP delay value) from the delivery of a right-ventricular stimulus until detection of the onset of a left-ventricular contraction in a far-field electrocardiogram, preferably recorded via a right-atrial electrode and the housing of the implant as the neutral electrode;

determines an average active filling phase (fill delay), e.g., as an empirically determined value; and calculates the AV time to be determined after detecting a natural right-atrial event using the following equation:

$$AV\ time = AS\ delay + full\ delay - VP\ delay.$$

Instead of the onset of a left-ventricular contraction in the far-field electrocardiogram as the end point of the period of time to be determined, the point in time of detection of a maximum of the ventricular total excitation may be detected as the end point in time of the period of time to be determined.

A suitable value for the average active filling phase (fill delay) is 100 ms.

An optimum AV time setting after delivery of a right-atrial stimulus may be determined by analogy with determination of the AV time after a right-atrial event, except that it is triggered by the atrial stimulus (AP delay).

As illustrated in FIG. 2 as an example, the AVD determination unit 92 is also designed to trigger the right-ventricular stimulation unit 56 at the end of an AV interval if it is not previously reset by a right-ventricular sense event detected by the right-ventricular sensing unit 58, so that ventricular stimuli are delivered only on demand. This AV interval preferably corresponds to the AV time determined previously plus a hysteresis interval.

LIST OF REFERENCE NUMERALS

| Reference numeral | Meaning |
| --- | --- |
| 10 | cardiac stimulator |
| 100 | external device |
| 12 | right-atrial electrode line |
| 14 | right-ventricular electrode line |
| 18 | heart |
| 20 | header (terminal housing) |
| 22 | housing |
| 24 | atrial tip electrode RA tip |
| 26 | atrial ring electrode RA ring |
| 28 | right atrium |
| 30 | right-ventricular tip electrode RV tip |
| 32 | right-ventricular ring electrode RV ring |
| 34 | right ventricle |
| 36 | right-ventricular shock coil RV shock |
| 38 | shock coil (SVG shock electrode) |
| 50 | right-ventricular shock pulse generator |
| 52 | SVC shock pulse generator |
| 54 | stimulation control unit |
| 56 | right-ventricular stimulation unit |
| 58 | right-ventricular sensing unit |
| 60 | right-atrial stimulation unit |

-continued

LIST OF REFERENCE NUMERALS

| Reference numeral | Meaning |
|---|---|
| 62 | right-atrial sensing unit |
| 72 | acceleration sensor |
| 80 | memory unit |
| 82 | timer |
| 84 | telemetry unit |
| 88 | switching unit |
| 90 | far-field electrocardiogram detection unit |
| 92 | evaluation unit |

What is claimed is:

1. An electromedical implant (10) comprising:
a housing (22) with an outside surface that is electrically conductive in at least some parts;
an electrode line;
at least one sensing unit (58; 62) coupled with said electrode line and configured to sense right atrial and right ventricular events;
at least two implantable electrodes;
a far-field electrocardiogram detection unit (90) connected to the at least two implantable electrodes, of which one is an electrode (30, 32; 24, 26) configured to be placed in a right atrium and one is configured to be placed in a right ventricle of a heart wherein each of said at least two implantable electrodes comprises a respective terminal coupled with said housing;
wherein the far-field electrocardiogram detection unit (90) is configured to record a far-field electrocardiogram via the at least two implantable electrodes;
a stimulation control unit (54);
a memory coupled with said stimulation control unit;
at least one stimulation pulse generator (60; 54);
wherein the stimulation control unit (54) and the at least one stimulation pulse generator (60; 54) are interconnected, so that the at least one stimulation pulse generator (60; 54) is configured to generate electric stimulation pulses controlled by the stimulation control unit (54) and is configured to deliver the electric stimulation pulses at certain points in time, as determined by the stimulation control unit (54), via the at least two implantable electrodes;
a far-field electrocardiogram evaluation unit (92);
wherein the far-field electrocardiogram detection unit (90) is connected to the far-field electrocardiogram evaluation unit (92); and,
wherein said far-field electrocardiogram evaluation unit (92) is configured to
detect a left-atrial or left ventricular contraction or both from the far-field electrocardiogram recorded by the far-field electrocardiogram detection unit (90) through comparison of morphology features of the far-field electrocardiogram with stored morphology features in the memory after a wavelet transformation on said far-field electrocardiogram and through comparison of wavelet coefficients with comparative coefficients stored in said memory after calculation of an average of multiple far-field electrocardiograms over a predefined number of individual heartbeats;
define an average active filling phase, or the fill delay, as an empirically determined value;
determine a ventricular pace or VP delay, from a delivery of a right-ventricular stimulus until detection of a start of a left-ventricular contraction in the far-field electrocardiogram, recorded via a right-atrial electrode selected from said at least two implantable electrodes, and the housing of the electromedical implant as a neutral electrode;
determine an atrial sense or AS delay value, between a detection of a natural right-atrial event and an end of a left-atrial excitation in the far-field electrocardiogram, recorded via a right-ventricular electrode selected from said at least two implantable electrodes, and the housing of the electromedical implant as the neutral electrode;
determine an atrial pace or AP delay as a period of time between a delivery of a right-atrial stimulation pulse and an end of the left-atrial excitation in the far-field electrocardiogram; and,
calculate the atrioventricular or AV time
after detection of a stimulated right-atrial event as:

$AV$ time=$AP$ delay+fill delay−$VP$ delay and after the detection of the natural right-atrial event as:

$AV$ time=$AS$ delay+fill delay−$VP$ delay.

2. The electromedical implant according to claim 1, wherein the empirically determined value for the average active filling phase, or the fill delay, is 100 ms.

3. A method for determining an atrioventricular or AV time comprising:
detecting a left-atrial or left ventricular contraction or both from a far-field electrocardiogram recorded by a far-field electrocardiogram detection unit (90) of an electromedical implant through comparison of morphology features of the far-field electrocardiogram with stored morphology features in a memory of the electromedical implant after a wavelet transformation on said far-field electrocardiogram and through comparison of wavelet coefficients with comparative coefficients stored in said memory after calculation of an average of multiple far-field electrocardiograms over a predefined number of individual heartbeats;
determining an atrial sense or AS delay value, between a detection of a natural right-atrial event and an end of a left-atrial excitation in the far-field electrocardiogram, recorded via a right-ventricular electrode and a housing of the electromedical implant as a neutral electrode;
determining a ventricular pace or VP delay value, from a delivery of a right-ventricular stimulus until a start of the left-ventricular contraction in the far-field electrocardiogram, recorded via a right-atrial electrode and the housing of an electromedical implant as the neutral electrode;
defining an average active filling phase, or fill delay, as an empirically determined value;
calculating an atrioventricular or AV time
after detection of a stimulated right-atrial event as:

$AV$ time=$AP$ delay+fill delay−$VP$ delay, and after the detection of the natural right-atrial event as:

$AV$ time=$AS$ delay+fill delay−$VP$ delay.

4. The method according to claim 3, further comprising determining the VP delay value, from the delivery of the right-ventricular stimulus until a detection of a maximum in a ventricular total complex in the far-field electrocardiogram.

5. The method according to claim 3, wherein the average active filling phase, or the fill delay, is 100 ms.

* * * * *